United States Patent [19]

Tóth et al.

[11] Patent Number: 4,564,630
[45] Date of Patent: Jan. 14, 1986

[54] CARBAMYLOXYBENZHYDROL DERIVATIVES AND PHARMACEUTICAL COMPOSITIONS CONTAINING THEM

[75] Inventors: Edit Tóth; József Törley; István Hajdu; Sánder Görög; Andrea Maderspach; György Hajós; László Szporny; András Jávor, all of Budapest, Hungary

[73] Assignee: Richter Gedeon Vegyeszeti Gyar Rt, Budapest, Hungary

[21] Appl. No.: 565,922

[22] Filed: Dec. 27, 1983

[30] Foreign Application Priority Data

Dec. 28, 1982 [HU] Hungary ................ 4191/82

[51] Int. Cl.⁴ .......... A61K 31/27; C07C 125/067; C07C 125/075
[52] U.S. Cl. .................... 514/478; 514/483; 514/490; 514/488; 560/32; 560/115; 560/163; 560/164
[58] Field of Search .......... 560/163, 164, 32, 115; 424/309, 311; 514/478, 483, 490, 488

[56] References Cited

U.S. PATENT DOCUMENTS 3,510,517  5/1970  Richter et al. ............ 560/164 X
3,985,811 10/1976  Fontanella et al. ........ 560/164 X
4,094,908  6/1978  Toth et al. .............. 260/501.18 X

OTHER PUBLICATIONS

Karrer, Organic Chemistry (1950), 211.
Bossinger, Chem. Abs., vol. 59 (1963), 9885f.
Chem. Abstracts 96:28204a.

Primary Examiner—Bernard Helfin
Attorney, Agent, or Firm—Karl F. Ross; Herbert Dubno

[57] ABSTRACT

The invention relates to new carbamyloxybenzhydrol derivatives of the formula (I)

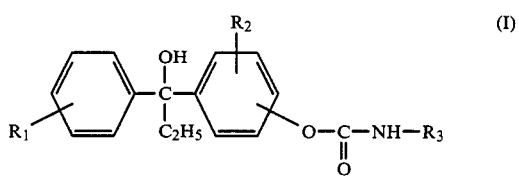

wherein
  $R_1$ is hydrogen, halogen, trihalomethyl, alkyl having from one to 4 carbon atoms or alkoxy having from one to 4 carbon atoms;
  $R_2$ is hydrogen or an $R_3$—NH—COO— group;
  $R_3$ is alkyl having from one to 6 carbon atoms, cycloalkyl having up to 7 carbon atoms, or phenyl, optionally substituted with one or more halogen(s).

The compounds of the formula (I) show antilipaemic activity and can therefore be used in therapy for treating hyperlipaemia and coronary diseases. Pharmaceutical compositions containing them as active ingredient are also within the scope of the invention.

4 Claims, No Drawings

CARBAMYLOXYBENZHYDROL DERIVATIVES AND PHARMACEUTICAL COMPOSITIONS CONTAINING THEM

The invention relates to new carbamates having antilipaemic activity. More particularly, the invention concerns new carbamyloxybenzhydrol derivatives of the formula (I)

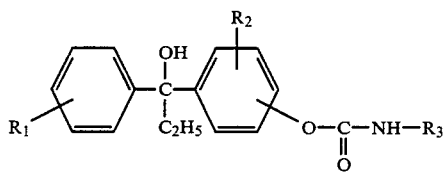

wherein
$R_1$ is hydrogen, halogen, trihalomethyl, alkyl having from one to 4 carbon atoms or alkoxy having from one to 4 carbon atoms;
$R_2$ is hydrogen or an $R_3$—NH—COO— group;
$R_3$ is alkyl having from one to 6 carbon atoms, cycloalkyl having up to 7 carbon atoms, or phenyl, optionally substituted with one or more halogen(s).

The new compounds possess valuable antilipaemic activity, and pharmaceutical compositions containing them as active ingredient are also within the scope of the invention.

The term "halogen" as used herein embraces all of the halogens, and may be fluorine, chlorine, bromine or iodine, preferably fluorine or chlorine.

The term "alkyl" refers to straight or branched chained aliphatic hydrocarbon groups, e.g. methyl, ethyl, n- or isopropyl, n-, sec- or tert-butyl, etc.

The term "alkoxy having from one to 4 carbon atoms" is used herein to refer to straight or branched chained alkoxy groups containing from one to 4 carbon atoms, preferably methoxy.

The trihalomethyl groups may contain any of the halogens listed above, preferably fluorine.

Compounds of analogous structure are disclosed for example in the following references: C.A. 22, 410[1]; 35, 1781[2]; 40, 4712[5]; 42, P 1015 b; 47, 9548 e; 50, 12390 c; 50, 2509 i; 55, 17915 e; 55, 15413 b; 75, P 103682 b; 76, P 119921 k; 82, 16477 g; 90, 52927 b. None of these citations does, however, mention any pharmaceutical activity of the disclosed compounds.

According to another aspect of the invention there is provided a process for the preparation of the compounds of the formula (I), wherein $R_1$, $R_2$ and $R_3$ each have the same meanings as defined above, which process comprises (a) esterifying a compound of the formula (II)

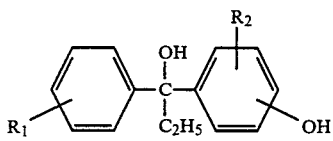

wherein $R_1$ is as defined above, and $R_2$ is hydrogen or hydroxy, with a reactive derivative of carbamic acid; or (b) reacting a compound of the formula (II) with phosgene and further reacting a compound of the formula (III)

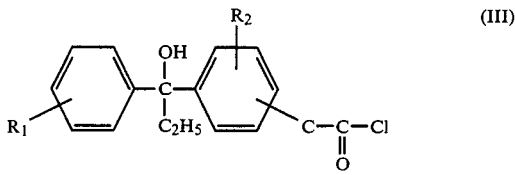

obtained, wherein in the formulae
$R_1$ is as defined above, and
$R_2$ is hydrogen or a chlorocarbonyloxy group (Cl—COO—),
with an amine of the formula (IV)

$$R_3-NH_2 \qquad (IV)$$

wherein $R_3$ is as defined above.

In process variant (a) according to the invention as a reactive derivative of carbamic acid for example carbamic acid halides of the formula (V)

$$R_3-NHCOX \qquad (V)$$

wherein $R_3$ is as defined above and X is halogen, preferably carbamic acid chlorides, or isocyanates of the formula (VI)

$$R_3-NCO \qquad (VI)$$

wherein $R_3$ is as defined above, are employed.

According to a preferred embodiment of process variant (a) a compound of the formula (II) is reacted with an isocyanate of the formula (VI), preferably in an inert organic solvent, in the presence of an inorganic or tertiary organic base. As an organic solvent for example aliphatic hydrocarbons such as dichloromethane, chloroform; aliphatic carboxylic acid nitriles, e.g. acetonitrile; aliphatic and alicyclic ethers such as diisopropyl ether, diethyl ether, tetrahydrofuran, dioxane; aliphatic and aromatic hydrocarbons such as ligroin, benzene, toluene, xylene; excess of the tertiary base, e.g. excess of pyridine or triethyl amine or a mixture of these solvents are used.

The reaction is substantially accelerated by inorganic or tertiary organic bases, therefore, the reaction is preferably performed in the presence of such bases. As an inorganic base preferably alkali metal carbonates, e.g. potassium carbonate, as a tertiary organic base for example pyridine, triethyl amine, 4-(dimethylamino)-pyridine, triethylene diamine, etc. are employed, in an at least catalytic amount.

The reaction temperature may be varied within a wide range, and generally is between 10° C. and 140° C., preferably 20° C. and 100° C.

The compounds of the formula (VI) are generally used in an at least equimolar amount related to the phenolic hydroxyl groups present in the compounds of the formula (II); it is, however preferred to use an excess amount.

The product of the reaction can be isolated by known techniques, e.g. extraction, evaporation, filtration, and can be purified in a known manner, for example by crystallization.

According to a preferred embodiment of process variant (b) a compound of the formula (II) is admixed with an aqueous alkali metal hydroxide, e.g. sodium or potassium hydroxide solution, and the reaction mixture is treated with a solution of phosgene in an inert organic solvent. As a solvent for example benzene, toluene, ether can be employed. The alkali metal hydroxide and phosgene are generally used in an equimolar amount related to the phenolic hydroxyl groups present in the corresponding compound of the formula (II). The reaction is exothermic. A solution of phosgene in an organic solvent is added to the sodium or potassium salt of a compound of the formula (II) with vigorous stirring, under cooling. The reaction temperature may range from −30° C. up to +30° C., and preferably is between −10° C. and +25° C. The chloroformate of the formula (III) obtained as a product of the reaction can be isolated and purified by known techniques, or can be further reacted with an amine of the formula (IV) without purification. The reaction is preferably carried out in an organic solvent, for example aromatic hydrocarbons such as benzene, toluene, or aliphatic or alicyclic ether such as diethyl ether, dioxane, tetrahydrofuran, but the reaction can be accomplished also in an aqueous medium.

The reaction temperature can be varied between −5° C. and +50° C., and preferably is between 0° C. and +25° C. The reaction is carried out in the presence of a base suitable for binding the acid formed in the reaction. For this purpose preferably inorganic or tertiary organic bases or an excess of the amine of the formula (IV) are employed. When the reaction is complete, the product is isolated, for example by pouring the reaction mixture onto water, and separating the product by solvent extraction. The organic phase is washed halogen-free with water, dried, the solvent is distilled off, and the residue is recrystallized.

The compounds of the formula (I) provided by the invention possess valuable pharmacological properties. In particular, they show antilipaemic activity and can therefore be used in therapy for treating hyperlipaemia, coronary diseases, etc.

In the blood lipids are linked with protein. According to their lipid content and electrophoretic mobility lipoproteins belong to four groups: chylomicrons, very low density lipoproteins (VLDL), low density lipoproteins (LDL) and high density lipoproteins (HDL).

Recent studies show that the increase of serum lipoprotein level is one of the pathogenetic factors in the development of arteriosclerosis, which plays an important role in cardiovascular diseases. Since in the most frequent hyperlipoproteinemias (types IIA, IIb and IV) an increase of cholesterol-rich LDL and triglyceride-rich VLDL is observed, these two types of lipoproteins are considered atherogenic. On the other hand, a large number of publications and epidemiological studies indicate that an increase of HDL level facilitates the intake of cholesterol from the peripheral tissues, its transport into the liver, its catabolism and elimination from the organism (G. J. Miller et al.: Lancet, 1 (1975) 16–19; N. E. Miller et al.: Lancet, 1 (1977) 965–968). Accordingly, HDL is considered an anti-arteriosclerosis factor. In view of the most recent research results, a new and active compound is expected not simply to reduce the cholesterol level but rather to decrease the quantity of atherogenic lipoproteins (LDL and VLDL) specifically and, as far as possible, to increase the proportion of HDL which facilitates the elimination of cholesterol. In addition, the compound must not be detrimental to the liver and should be devoid of any effect resulting in the increase of the weight of liver.

The activity of the new compounds provided by the present invention was examined by the following tests.

(a) Cholesterol Administration Test on Rats

Tests were carried out on male Wistar rats, each weighing 140 to 160 g. Groups of eight were fed with a "LATI rat food" containing 1.5% of cholesterol, 0.5% of cholic acid and 5% of hardened fats, for 7 days. The animals were given food and water ad libitum during the whole test. In the first three days the animals were not subjected to any pharmaceutical treatment, while from the fourth day they were treated four-times with 30 and 100 mg./kg. doses of the test compounds, orally. On the eighth day, after fasting for 18 hour, the animals were allowed to bleed to death. The blood samples were centrifuged and from the serum the total amount of cholesterol (Tlatkis, A., Zak, B., Boyle, A. J.: J. Lab. Clin. Med. 41, 486 (1953)), triglyceride (Van Handel E., Zilversmit, D. B.: J. Lab. Clin. Med., 50, 152 (1957)) and the quantity of heparin precipitating lipoproteins (HPL), which contains the total amount of VLDL and LDL (Schurr, P. E., Schultz, J. R., Day, C. E.: Atherosclerosis Drug Discovery, Ed. C. E. Day, Plenum Press, New York, 215–229 (1975)), were determined.

(b) Tests on Mormolipidemic Rats

Tests were carried out on male Wistar rats, weighing 140 to 160 g, each. Groups of six were fed with a "LATI rat food". Food and water were given ad libitum during the whole test. The animals were treated with 100 mg./kg. oral doses of the test compounds for five days. The last treatment was carried out two hours before killing the aminals, which were fasted 18 hours before their death. The rats were then allowed to bleed to death through the femoral vein. The blood samples were centrifuged and from the serum the quantity of heparin precipitating lipoproteins (as described in test a)) was determined. The heparin precipitating lipoproteins were then separated, and from the supernatant the cholesterol concentration of HDL was determined (Warnick, G. R. et al.: J. Lipid. Res., 19 (1) 65 (1978)).

As a reference compound Clofibrate (Miscleron ®) was employed, which is widely used in therapy.

TABLE I

| | | Cholesterol administration test | | | | | |
|---|---|---|---|---|---|---|---|
| | Dose | Serum | | | | | |
| | p.o. | cholesterol | | triglyceride | | HPL | |
| Compound | mg/kg | mg % | change % | mg % | change % | $A_{680} \times 10^3$ | change % |
| Control | — | 546.3 | — | 132.0 | — | 871.3 | — |
| A | 30 | 347.7 | −36.4 | 85.4 | −35.3 | 838.3 | −3.8 |
| | 100 | 382.0 | −30.1 | 64.3 | −51.2 | 773.3 | −11 |
| B | 30 | 445.2 | −18.5 | 82.1 | −37.8 | 741.7 | −14.9 |
| | 100 | 325.7 | −40.3 | 76.7 | −41.9 | 662.5 | −24.0 |
| Clofibrate | 100 | 457.9 | −16.2 | 101.6 | −23.0 | 1019.4 | +17.0 |

A = 3-(trifluoromethyl)-4'-(N—propylcarbamyloxy)-α-ethyl-benzhydrol
B = 3-(trifluoromethyl)-4'-(N—butyl-carbamyloxy)-α-ethyl-benzhydrol

TABLE II

| | Dose p.o. mg/kg | Normolipidemic test | | | |
|---|---|---|---|---|---|
| | | HPL | | HDL-cholesterol | |
| Compound | | $A_{680} \times 10^3$ | change % | mg % | change % |
| Control | — | 125.0 | — | 41.8 | — |
| A | 100 | 103.0 | −27.6 | 68.8 | +64.6 |
| B | 100 | 86.6 | −30.7 | 56.8 | +36 |
| Clofibrate | 100 | 111.0 | −11.2 | 35.7 | −14.6 |

As appears from the data set forth in the above tables, the cholesterol and triglyceride level decreasing activity of the test compounds of the formula (I) is superior to the activity of Clofibrate. The compounds provided by the invention alter the distribution of the cholesterol content of lipoproteins, namely, they reduce the quantity of aterogenic lipoproteins, whereas they increase the cholesterol content of HDL, which eliminates cholesterol from the organism, by 64.6% and 36%, respectively. This effect of the instant compounds is completely different from the effect of Clofibrate, which is known to decrease all lipoprotein fractions including HDL, although it would be desirable to increase the latter's amount (K. Müller; Abstracts of Sixth Int. Symp. on Drugs Affecting Lipid Metabolism, Philadelphia, PA, 64 (1977)).

A further advantage of the compounds of the formula (I) over Clofibrate consists in the fact that they are devoid of any liver injuring effect; they do not increase the weight of liver in a dose of 100 mg./kg. in contrast to Clofibrate which results in a 16 to 20% weight increase related to the control animals when administered in the same dose.

The pharmacologically active compounds according to the invention can be used in therapy in the form of pharmaceutical compositions, which are formulated as preparations suitable for oral, rectal and/or parenteral administration. For oral administration tablets, dragees or capsules are prepared. The oral formulations contain as a vehicle e.g. lactose or starch, as an excipient or a granulation aid e.g. gelatine, carboxymethyl cellulose sodium, methyl cellulose, polyvinyl pyrrolidone or starch gum, as a disintegrating substance e.g. potato starch or microcrystalline cellulose, ultraamylopectin or formaldehyde casein, etc. The formulations may also contain adhesives and lubricants such as talc, colloidal silica, stearin, calcium or magnesium stearate, etc.

Tablets are prepared for example by wet granulation and subsequent pressing. A mixture of the active ingredient and the vehicle and optionally a part of the disintegrating agent are granulated with an aqueous, alcoholic or aqueous-alcoholic solution of the excipients in suitable equipment, and the granulate is dried. The remaining portion of the disintegrating substance, lubricant, antiadhesive or optional further additives is then added to the granules, and the mixture is pressed to tablets. If desired, the tablets are prepared with a dividing line, which facilitates administration. Tablets can be prepared also from a mixture of the active ingredient and suitable additives by direct pressing.

If desired, the tablets can be converted into dragees, using protecting, flavoring agents and pigments generally known for the preparation of pharmaceutical compositions, e.g. sugar, cellulose derivatives (methyl or ethyl cellulose, carboxymethyl cellulose sodium, etc.), polyvinylpyrrolidone, calcium phosphate, calcium carbonate, food pigments, food oil varnishes, aroma substances, iron oxide pigments, etc.

Capsules are prepared by filling a mixture of the active ingredients and additives into suitable capsules.

For rectal administration the compositions are formulated as suppositories, which contain in addition to the active ingredient a carrier mass, called adeps pro suppository. Suitable carriers include vegetable fats, e.g. hardened vegetable oils, triglycerides of fatty acids having from 12 to 18 carbon atoms, preferably Witepsol (a registered trademark). The active ingredient is homogeneously distributed in the melted carrier mass, and suppositories are prepared by casting.

For parenteral administration injectable preparations are prepared. To prepare an injectable solution the active ingredients is dissolved in distilled water and/or various organic solvent, e.g. glycol ethers, optionally in the presence of dissolution aids, e.g. polyoxyethylene sorbitan monolaurate, monooleate or monostearate (Tween 20, Tween 60, Tween 80). The injectable solutions may contain also various additives, e.g. preserving agents such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind metal traces such as ethylene diamine tetraacetate, buffers to adjust the pH and optionally local anaesthetics such as lidocaine. The injectable solutions are filtered, filled into ampoules and sterilized. The daily does, depending on the state of the patient, varies between 100 and 2500 mg., preferably 200 and 1000 mg., which is preferably administered in more smaller doses.

The invention will be further illustrated by the following Examples but it is not intended to limit the scope of the invention to the Examples.

EXAMPLE 1

3-Trifluoromethyl-4'-(N-butyl-carbamyloxy)-α-ethyl-benzhydrol 8.9 g. of 3-trifluoromethyl-4'-hydroxy-α-ethyl-benzhydrol, 3.3 g. of n-butyl-isocyanate and 0.06 ml. of triethyl amine in 45 ml. of dry benzene are heated up to 50° C. under stirring, and the reaction mixture is kept at the same temperature for one additional hour. The progress of the reaction is monitored by thin layer chromatography. When the reaction is complete, the mixture is cooled to room temperature, the benzene solution is shaken with a 5% aqueous potassium hydroxide solution and washed to neutral with water. The organic phase is dried over anhydrous magnesium sulfate, filtered, and the solvent is distilled off under reduced pressure. The solid residue is crystallized from a mixture of ethyl acetate and n-hexane. 11.4 g. of the named compound are obtained, melting at 99° to 100° C.

Analysis for $C_{21}H_{24}F_3NO_3$: Calculated: C 63.78%, H 6.12%, F 14.41%, N 3.54%; Found: C 63.85%, H 6.30%, F 14.60%, N 3.47%.

EXAMPLE 2

4-Chloro-4'-(N-butyl-carbamoyloxy)-α-ethyl-benzhydrol 7.9 g. of 4-chloro-4'-hydroxy-α-ethyl-benzhydrol, 3.3 g. of n-butyl-isocyanate and 0.3 ml. of triethyl amine are dissolved in 40 ml. of dry tetrahydrofurane under stirring at 25° C., and the solution is allowed to stand at this temperature for 20 hours. When the reaction is complete, tetrahydrofurane is distilled off under reduced pressure, the residue is taken up in ether, the ethereal solution is shaken with a 5% aqueous sodium hydroxide solution and washed to neutral with water. The organic phase is dried over anhydrous magnesium sulfate, filtered and ether is distilled off in vacuo. Crystallization of the residue from a mixture of n-hexane and ethyl acetate yields 9.3 g. of the named compound, which melts at 78° to 79° C.

Analysis for $C_{20}H_{24}ClNO_3$: Calculated: C 66.38%, H 6.68%, Cl 9.80%, N 3.87%; Found: C 66.48%, H 6.74%, Cl 9.72%, N 3.98%.

EXAMPLE 3

3-Trifluoromethyl-2',4'-bis(N-butyl-carbamyloxy)-α-ethyl-benzhydrol 6.2 g. of 3-trifluoromethyl-2',4'-dihydroxy-α-ethyl-benzhydrol, 4.4 g. of butyl isocyanate and 0.06 g. of 4-dimethylamino-pyridine in 40 ml. of dichloromethane are refluxed for 60 minutes. The reaction mixture is cooled down, and the organic phase is extracted with a 5% aqueous potassium hydroxide solution and washed to neutral with water. The organic phase is dried over anhydrous magnesium sulfate, filtered and solvent is distilled off under reduced pressure. Crystallization of the residue from toluene yields 8.7 g. of the end product, which melts at 110° to 111° C.

Analysis for $C_{26}H_{33}F_3N_2O_5$: Calculated: C 61.16%, H 6.51%, F 11.16%, N 5.49%; Found: C 61.33%, H 6.64%, F 11.28%, N 5.65%.

EXAMPLE 4

4-Fluoro-4'-(N-propyl-carbamyloxy)-α-ethyl-benzhydrol 12.3 g. of 4-fluoro-4'-hydroxy-α-ethyl-benzhydrol, 4.68 g. of n-propyl-isocyanate and 0.7 g. of anhydrous, powdered potassium carbonate in 61 ml. of acetonitrile containing 15 μlit. of a 50% aqueous ethanol solution are refluxed under stirring. When the reaction is complete, the reaction mixture is cooled to room temperature, potassium carbonate is filtered off and acetonitrile is distilled off under reduced pressure. The residue is dissolved in benzene, the benzene solution is shaken with a 5% aqueous sodium hydroxide solution and washed to neutral with water. The organic phase is dried over anhydrous magnesium sulfate, filtered, and benzene is distilled off under reduced pressure. Crystallization of the residue from a mixture of ethyl acetate and n-hexane yields 13.6 g. of the desired compound, melting at 107° to 108° C.

Analysis for $C_{19}H_{22}FNO_3$: Calculated: C 66.86%, H 6.69%, F 5.73%, N 4.23%; Found: C 68.71%, H 6.84%, F 5.90%, N 4.33%.

The following compounds can be prepared essentially as described in Examples 1 ∝ 4, by proper selection of the starting substances.

3-Trifluoromethyl-4'-[N-(3,4-dichlorophenyl)-carbamyloxy]-α-ethyl-benzhydrol, melting point: 58° to 59° C.

Analysis for $C_{23}H_{18}Cl_2F_3NO_3$: Calculated: C 57.04%, H 3.75%, F 11.77%, Cl 14.64%, N 2.89%; Found: C 57.23%, H 3.88%, F 11.63%, Cl 14.81%, N 3.14%.

4-Chloro-4'-(N-ethyl-carbamyloxy)-α-ethyl-benzhydrol, melting point: 91° to 92° C.

Analysis for $C_{18}H_{20}ClNO_3$: Calculated: C 64.76%, H 6.04%, Cl 10.62%, N 4.20%; Found: C 64.88%, H 6.13%, Cl 10.85%, N 4.35%.

3-Chloro-4'-(N-propyl-carbamyloxy)-α-ethyl-benzhydrol, melting point: 81° to 82° C.

Analysis for $C_{19}H_{22}ClNO_3$: Calculated: C 65.60%, H 6.37%, Cl 10.19%, N 4.03%; Found: C 65.64%, H 6.44%, Cl 10.38%, N 4.23%.

2-Methoxy-4'-(N-methyl-carbamyloxy)-α-ethyl-benzhydrol, melting point: 111° to 112° C.

Analysis for $C_{18}H_{21}NO_4$: Calculated: C 68.55%, H 6.71%, N 4.44%; Found: C 68.63%, H 6.58%, N 4.57%.

3-Trifluoromethyl-4'-(N-propyl-carbamyloxy)-α-ethyl-benzhydrol, melting point: 95° to 96° C.

Analysis for $C_{20}H_{22}F_3NO_3$: Calculated: C 62.98%, H 5.81%, F 14.95%, N 3.67%; Found: C 63.12%, H 5.74%, F 15.17%, N 3.55%.

3-Chloro-4'-(N-ethyl-carbamyloxy)-α-ethyl-benzhydrol, melting point: 82° to 83° C.

Analysis for $C_{18}H_{20}ClNO_3$: Calculated: C 64.76%, H 6.04%, Cl 10.62%, N 4.20%; Found: C 64.66%, H 6.12%, Cl 10.44%, N 4.23%.

2-Methoxy-4'-(N-propyl-carbamyloxy)-α-ethyl-benzhydrol, melting point: 105° to 106° C.

Analysis for $C_{20}H_{25}NO_4$: Calculated: C 69.94%, H 7.34%, N 4.08%; Found: C 70.12%, H 7.51%, N 4.23%.

4-Chloro-4'-(N-methyl-carbamyloxy)-α-ethyl-benzhydrol, melting point: 84° to 85° C.

Analysis for $C_{17}H_{18}ClNO_3$: Calculated: C 63.85%, H 5.67%, Cl 11.09%, N 4.38%; Found: C 64.01%, H 5.78%, Cl 11.15%, N 4.43%.

3-Chloro-4'-(N-methyl-carbamyloxy)-α-ethyl-benzhydrol, melting point: 93° to 94° C.

Analysis for $C_{17}H_{18}ClNO_3$: Calculated: C 63.85%, H 5.67%, Cl 11.09%, N 4.38%; Found: C 63.67%, H 5.74%, Cl 11.20%, N 4.23%.

3-Trifluoromethyl-2',4'-bis(N-propyl-carbamyloxy)-α-ethyl-benzhydrol, melting point: 123° C.

Analysis for $C_{24}H_{29}F_3N_2O_5$: Calculated: C 59.74%, H 6.06%, F 11.81%, N 5.81%; Found: C 59.65%, H 6.18%, F 11.93%, N 5.87%.

2-Methoxy-4'-(N-ethyl-carbamyloxy)-α-ethyl-benzhydrol, melting point: 121° to 122° C.

Analysis for $C_{19}H_{23}NO_4$: Calculated: C 69.28%, H 7.04%, N 4.25%; Found: C 69.43%, H 7.10%, N 4.44%.

3-Trifluoromethyl-2'-(N-butyl-carbamyloxy)-α-ethyl-benzhydrol, melting point: 84° to 85° C.

Analysis for $C_{21}H_{24}F_3NO_3$: Calculated: C 63.78%, H 6.12%, F 14.41%, N 3.54%; Found: C 63.77%, H 6.07%, F 14.23%, N 3.71%.

3-Trifluoromethyl-4'-(N-methyl-carbamyloxy)-α-ethyl-benzhydrol, melting point: 158° to 159° C.

Analysis for $C_{18}H_{18}F_3NO_3$: Calculated: C 61.18%, H 5.13%, F 16.13%, N 3.96%; Found: C 61.30%, H 5.18%, F 16.33%, N 4.11%.

3-Chloro-4'-(N-butyl-carbamyloxy)-α-ethyl-benzhydrol, melting point: 84° to 85° C.

Analysis for $C_{20}H_{24}ClNO_3$: Calculated: C 66.38%, H 6.68%, Cl 9.80%, N 3.87%; Found: C 66.27%, H 6.81%, Cl 9.87%, N 3.78%.

3-Trifluoromethyl-4'-(N-ethyl-carbamyloxy)-α-ethyl-benzhydrol, melting point: 110° to 111° C.

Analysis for $C_{19}H_{20}F_3NO_3$: Calculated: C 62.12%, H 5.49%, F 15.52%, N 3.81%; Found: C 62.17%, H 5.66%, F 15.68%, N 3.74%.

3-Trifluoromethyl-2'-(N-propyl-carbamyloxy)-α-ethyl-benzhydrol, melting point: 49° to 50° C.

Analysis for $C_{20}H_{22}F_3NO_3$: Calculated: C 62.98%, H 5.81%, F 14.95%, N 3.67%; Found: C 62.81%, H 5.96%, F 15.14%, N 3.76%.

3-Trifluoromethyl-4'-(N-phenyl-carbamyloxy)-α-ethyl-benzhydrol, melting point: 91° to 92° C.

Analysis for $C_{23}H_{20}F_3NO_3$: Calculated: C 66.50%, H 4.85%, F 13.72%, N 3.37%; Found: C 66.66%, H 5.03%, F 13.49%, N 3.44%.

3-Trifluoromethyl-4'-(N-cyclohexyl-carbamyloxy)-α-ethyl-benzhydrol, melting point: 89° to 90° C.

Analysis for $C_{23}H_{26}F_3NO_3$: Calculated: C 65.54%, H 6.22%, F 13.52%, N 3.32%; Found: C 65.73%, H 6.18%, F 13.74%, N 3.47%.

4-Fluoro-4'-(N-butyl-carbamyloxy)-α-ethyl-benzhydrol, melting point: 104° to 105° C.

Analysis for $C_{20}H_{24}FNO_2$: Calculated: C 69.54%, H 7.00%, F 5.50%, N 4.05%; Found: C 69.73%, H 7.11%, F 5.45%, N 4.18%.

2-Methoxy-4'-(N-tert-butyl-carbamyloxy)-α-ethyl-benzhydrol, melting point: 102° to 103° C.

Analysis for $C_{21}H_{27}NO_4$: Calculated: C 70.56%, H 7.61%, N 3.92%; Found: C 70.71%, H 7.53%, N 4.14%.

3-Trifluoromethyl-4'-(N-tert-butyl-carbamyloxy)-α-ethyl-benzhydrol, melting point: 130° to 131° C.

Analysis for $C_{21}H_{24}F_3NO_3$: Calculated: C 63.78%, H 6.12%, F 14.41%, N 3.54%; Found: C 63.77%, H 6.22%, F 14.57%, N 3.58%.

EXAMPLE 5

4-Chloro-4'-(N-propyl-carbamyloxy)-α-ethyl-benzhydrol

To a solution of 5.25 g. of 4-chloro-4'-hydroxy-α-ethyl-benzhydrol in 15.2 ml. of a 5% by weight aqueous sodium hydroxide solution a solution of 1.98 g. of phosgene in 12 ml. of toluene is added dropwise, at 0° C., under vigorous stirring. The reaction mixture is stirred for two additional hours, it is then warmed to room temperature, and the phases are separated. The organic phase is shaken with a 5% aqueous potassium hydroxide solution and washed to neutral with water. The toluene solution is dried over anhydrous sodium sulfate, and the solvent is distilled off in vacuo. The residue is dissolved in 40 ml. of dry ether, and the solution is added dropwise to a solution of 2.36 g. of propyl amine in 20 ml. of dry ether, at a temperature between 0° C. and +5° C. Thereafter, the reaction mixture is stirred at room temperature for 16 hours. The ethereal solution is washed to chloride ion-free with water, dried over anhydrous magnesium sulfate and ether is distilled of in vacuo. Crystallization of the residue from a mixture of n-hexane and ethyl acetate yields the named compound. Melting point: 71° to 72° C.

Analysis for $C_{19}H_{22}ClNO_3$: Calculated: C 65.60%, H 6.37%, Cl 10.19%, N 4.03%; Found: C 65.54%, H 6.32%, Cl 10.35%, N 4.21%.

EXAMPLE 6

The new compounds according to the invention can for example be converted into the following pharmaceutical compositions.

Tablets

Composition of a single tablet:

| | |
|---|---|
| active ingredient | 100.0 mg. |
| lactose | 184.0 mg. |
| potato starch | 80.0 mg. |
| polyvinyl pyrrolidone | 8.0 mg. |
| talc | 12.0 mg. |
| magnesium stearate | 2.0 mg. |
| aerosil (colloidal $SiO_2$) | 2.0 mg. |
| ultraamylopectin | 12.0 mg. |

From the above ingredients 400-mg. tablets are prepared by wet granulation and subsequent pressing. Active ingredient: 3-(trifluoromethyl)-4'-(N-propyl-carbamyloxy)-α-ethyl-benzhydrol.

Dragees

Tablets as described above are coated with a layer prepared from sugar and talc in a known manner. Dragees are polished with a mixture of bee wax and carnauba wax. Weight of a dragee: 500.0 mg.

Capsules

| Composition of a capsule: | |
|---|---|
| active ingredient | 50.0 mg. |
| lactose | 100.0 mg. |
| talc | 2.0 mg. |
| potato starch | 30.0 mg. |
| cellulose (microcrystalline) | 3.0 mg. |

The active ingredient is thoroughly admixed with the additives, the mixture is passed through a 0.32-mm. sieve, and filled into hard gelatine capsules size 4. Active ingredient: 3-(trifluoromethyl)-4'-(N-butyl-carbamyloxy)-α-ethyl-benzhydrol.

Suppositories

| Composition of a suppository: | |
|---|---|
| active ingredient | 100.0 mg. |
| lactose | 200.0 mg. |
| basic substance (e.g. Witepsol H) | 1700.0 mg. |

The basic substance is melted and then cooled to 35° C. The active ingredient is thoroughly blended with the lactose, and the mixture is homogenized in the basic substance with a homogenizer. The obtained mass is poured into cool molds. One suppository weights 2000 mg. Active ingredient: 3-(trifluoromethyl)-4'-(N-propyl-carbamyloxy)-α-ethyl-benzhydrol.

We claim:

1. A compound of the formula (I)

$$R_1 \text{-} \underset{\underset{C_2H_5}{|}}{\overset{\overset{OH}{|}}{C}} \text{-} \underset{R_2}{\text{-}} \text{-} O\text{-}\underset{\underset{O}{\|}}{C}\text{-}NH\text{-}R_3 \quad (I)$$

wherein
$R_1$ is hydrogen, halogen, trihalomethyl, alkyl having from one to 4 carbon atoms or alkoxy having from one to 4 carbon atoms;
$R_2$ is hydrogen or an $R_3$—NH—COO— group;
$R_3$ is alkyl having from one to 6 carbon atoms, cycloalkyl having up to 7 carbon atoms, or phenyl which can be substituted with at least one halogens.

2. A compound selected from the following group:

3-trifluoromethyl-4'-(N-butyl-carbamyloxy)-α-ethyl-benzhydrol, 4-chloro-4'-(N-butyl-carbamyloxy)-α-ethyl-benzhydrol, 3-trifluoromethyl-2',4'-bis(N-butyl-carbamyloxy)-α-ethyl-benzhydrol, 4-fluoro-4'-(N-propyl-carbamyloxy)-α-ethyl-benzhydrol, 3-trifluoromethyl-4'-[N-(3,4-dichlorophenyl)-carbamyloxy]-α-ethyl-benzhydrol, 4-chloro-4'-(N-ethyl-carbamyloxy)-α-ethyl-benzhydrol, 3-chloro-4'-(N-propyl-carbamyloxy)-α-ethyl-benzhydrol, 2-methoxy-4'-(N-methyl-carbamyloxy)-α-ethyl-benzhydrol, 3-trifluoromethyl-4'-(N-propyl-carbamyloxy)-α-ethyl-benzhydrol, 3-chloro-4'-(N-ethyl-carbamyloxy)-α-ethyl-benzhydrol, 2-methoxy-4'-(N-propyl-carbamyloxy)-α-ethyl-benzhydrol, 4-chloro-4'-(N-methyl-carbamyloxy)-α-ethyl-benzhydrol, 3-chloro-4'-(N-methyl-carbamyloxy)-α-ethyl-benzhydrol, 3-trifluoromethyl-2',4'-bis(N-propyl-carbamyloxy)-α-ethyl-benzhydrol, 2-methoxy-4'-(N-ethyl-carbamyloxy)-α-ethyl-benzhydrol, 3-trifluoromethyl-2'-(N-butyl-carbamyloxy)-α-ethyl-benzhydrol, 3-trifluoromethyl-4'-(N-methyl-carbamyloxy)-α-ethyl-benzhydrol, 3-chloro-4'-(N-butyl-carbamyloxy)-α-ethyl-benzhydrol, 3-trifluoromethyl-4'-(N-ethyl-carbamyloxy)-α-ethyl-benzhydrol, 3-trifluoromethyl-2'-(N-propyl-carbamyloxy)-α-ethyl-benzhydrol, 3-trifluoromethyl-4'-(N-phenyl-carbamyloxy)-α-ethyl-benzhydrol, 3-trifluoromethyl-4'-(N-cyclohexyl-carbamyloxy)-α-ethyl-benzhydrol, 4-fluoro-4'-(N-butyl-carbamyloxy)-α-ethyl-benzhydrol, 2-methoxy-4'-(N-tert-butyl-carbamyloxy)-α-ethyl-benzhydrol, 3-trifluoromethyl-4'-(N-tert-butyl-carbamyloxy)-α-ethyl-benzhydrol, and 4-chloro-4'-(N-propyl-carbamyloxy)-α-ethyl-benzhydrol.

3. An antilipaemic composition containing a pharmaceutically effective amount of a compound of the formula (I) as defined in claim 1, together with a pharmaceutically acceptable carrier and/or auxiliary substance.

4. A method of treating hyperlipaemia in a mammalian subject which comprises treating said subject with a pharmaceutically effective amount of a compound of the Formula (I) defined in claim 1.

* * * * *